United States Patent [19]

Benderev et al.

[11] Patent Number: 5,439,467

[45] Date of Patent: Aug. 8, 1995

[54] SUTURE PASSER

[75] Inventors: Theodore V. Benderev, Laguna Hills; Neil H. Naves; Mark J. Legome, both of Mission Viejo, all of Calif.

[73] Assignee: Vesica Medical, Inc., San Clemente, Calif.

[21] Appl. No.: 78,730

[22] Filed: Jun. 17, 1993

Related U.S. Application Data

[60] Division of Ser. No. 862,847, Apr. 3, 1992, which is a continuation-in-part of Ser. No. 801,747, Dec. 3, 1991, abandoned.

[51] Int. Cl.$^6$ ............................................. A61B 17/04
[52] U.S. Cl. ................................... 606/139; 606/144; 606/148; 606/167
[58] Field of Search ............... 606/144, 139, 167, 168, 606/185, 182, 148

[56] References Cited

U.S. PATENT DOCUMENTS

| | | |
|---|---|---|
| 2,738,790 | 3/1956 | Todt, Sr. et al. |
| 3,995,619 | 12/1976 | Glatzer . |
| 4,172,458 | 10/1979 | Pereyra . |
| 4,957,498 | 9/1990 | Caspari et al. . |
| 5,085,661 | 2/1992 | Moss ................................. 606/139 |
| 5,188,636 | 2/1993 | Fedotov ............................ 606/139 |
| 5,281,237 | 1/1994 | Gimpelson ........................ 606/139 |

FOREIGN PATENT DOCUMENTS

| | | |
|---|---|---|
| 2305815 | 8/1974 | Germany . |
| 1225547 | 4/1986 | Switzerland . |

OTHER PUBLICATIONS

*A Simplified Surgical Procedure for the Correction of Stress Incontinence in Women*, by Armand J. Pereyra, M.D., F.A.C.S. in West. J. Surg., Obst. & Gynec. Jul.-Aug., 1959.
*Marshall-Marchetti Procedure Modification*, by Charles F. McKiel, Jr., et al. in The Journal of Urology 1966.
*Endoscopic Suspension of the Vesical Neck for Urinary Incontinence*, by Thomas A. Stamey, M.D. in Surgery, Gynecology & Obstetrics Apr. 1973 vol. 136.
*Modified Bladder Neck Suspension For Female Stress Incontinence*, by Shlomo Raz, M.D. in Urology Jan. 1981 vol. XVII No. 1.
*Peripubic Urethropexy for Urinary Stress Incontinence in Women*, by Chester C. Winter, M.D. in Urology Oct. 1982 vol. XX No. 4.
*Female Urinary Incontinence*, by George D. Webster in Urologic Surgery 3rd Edition 1983.
*A Comparison of Endoscopic Suspension of the Vesical Neck with Suprapubic Vesicourethropexy for Treatment of Stress Urinary Incontinence*, by Julia R. Spencer et al. in The Journal of Urology vol. 137 Mar. 1987.
*No-Incision Pubovaginal Suspension for Stress Incontinence*, by Ruben F. Gittes et al. in The Journal of Urology vol. 138 Sep. 1987.
*Bone Fixation Technique for Transvaginal Needle Suspension*, by Gary E. Leach, M.D. in Urology vol. XXXI No. 5 May 1988.
*Review of an 8-Year Experience with Modifications of Endosonic Suspension of the Blasser Neck for Female Stress Urinary Incontinence*, by Kevin R. Loughlin et al. in The Journal of Urology vol. 143 Jan. 1990.
*The Sling Procedure for Urinary Stress Incontinence*, by Edward J. McGuire, M.D. in Profiles in Urology undated.
*Experience with a Simplified Technique for the Treatment of Female Stress Urinary Incontinence*, by R. O. Parra and L. Shaker, British Journal of Urology 66, 615-617 (1990).

Primary Examiner—Gary Jackson
Attorney, Agent, or Firm—Knobbe, Martens, Olson & Bear

[57] ABSTRACT

A suture passer of the type adapted for releasably retaining a suture is disclosed. The suture passer has a handle and an elongate tubular probe guide extending in a distal direction from the handle. The tubular probe guide can be straight or curved. An elongate probe is axially movably disposed within the tubular probe guide, for motion between at least one retracted position and an extended position in which the sharpened distal tip of the probe is exposed. The probe has a recess, which cooperates with an opening on the tubular guide for receiving a suture.

18 Claims, 2 Drawing Sheets

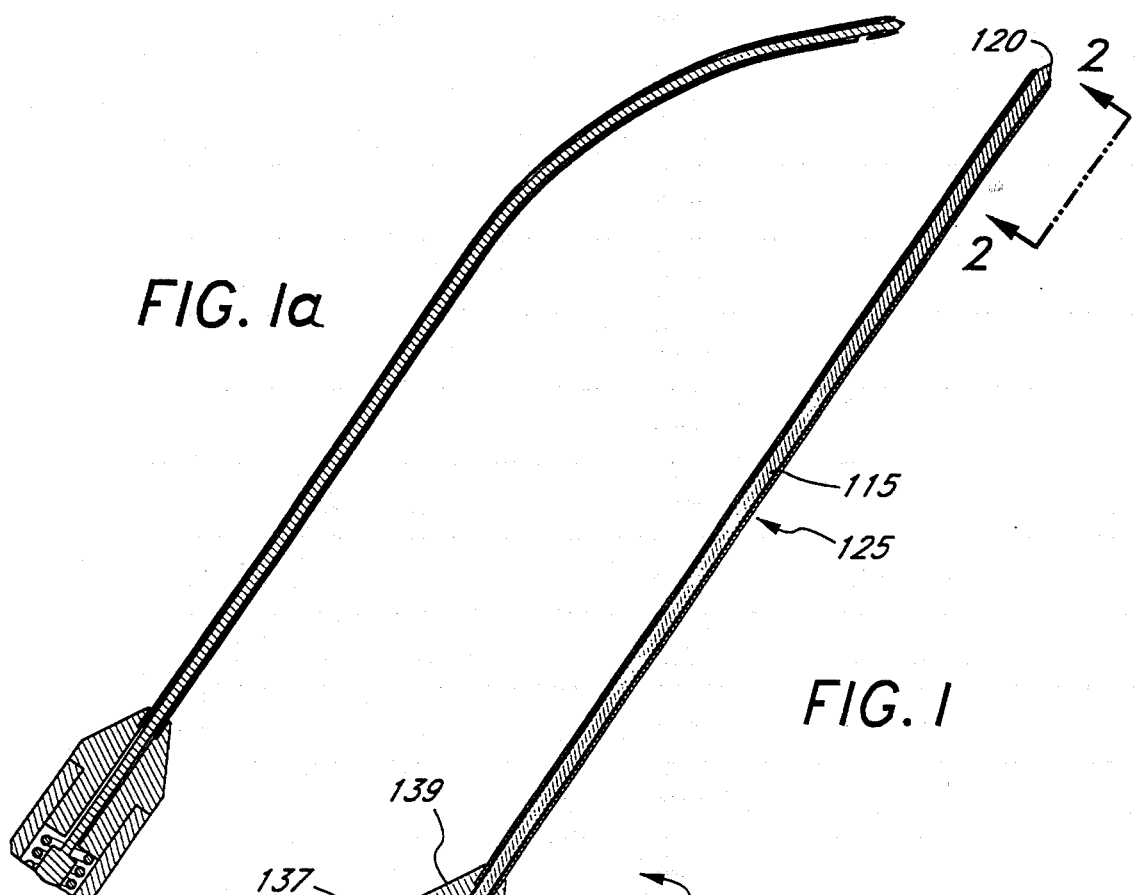
FIG. 1a
FIG. 1
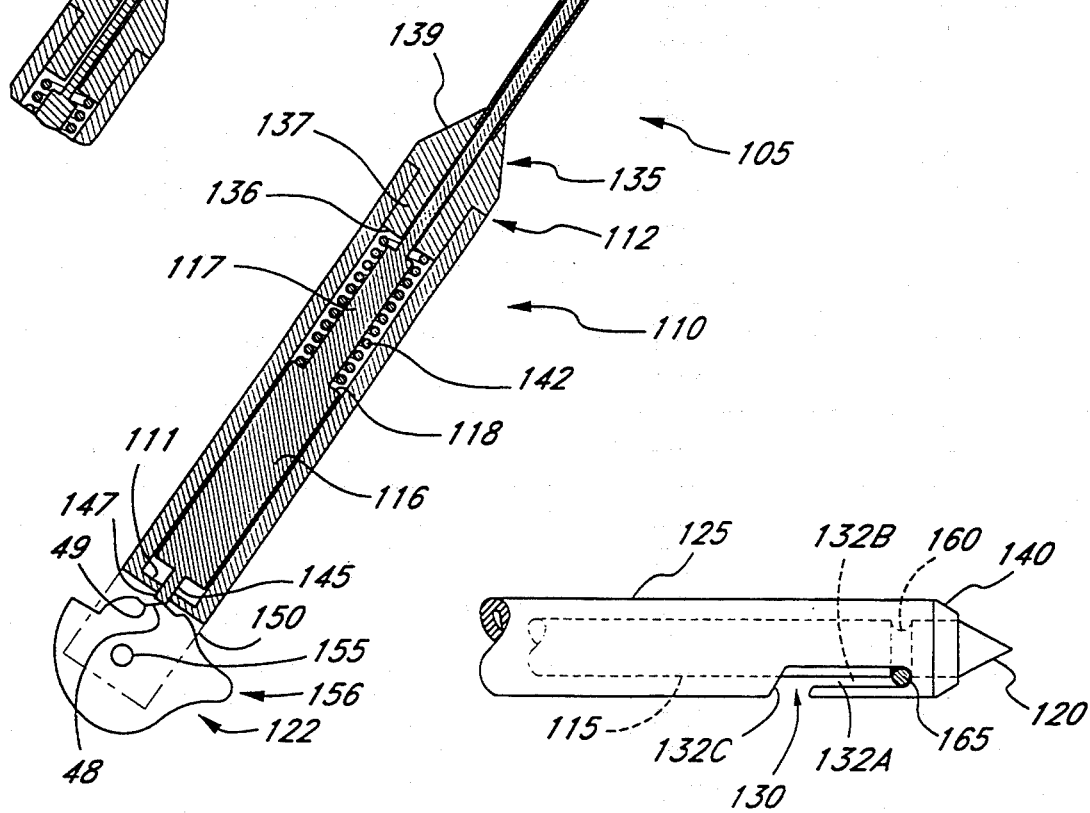
FIG. 2

SUTURE PASSER

This application is a divisional of application Ser. No. 07/862,847, filed Apr. 3, 1992; pending which is a Continuation-in-Part of Ser. No. 07/801,747, filed Dec. 3, 1991 now abandoned.

BACKGROUND OF THE INVENTION

The present invention relates to the treatment of stress urinary incontinence "SUI," and in particular, to improved, methods and surgical devices for the surgical treatment of SUI in females. The devices disclosed herein are additionally useful in a wide variety of other surgical procedures.

Genuine stress incontinence is the involuntary loss of urine due to a sudden rise in intra-abdominal pressure. It has been estimated that between 40% and 50% of young, healthy nulliparous women admit to occasional mild stress incontinence; however, at least 80% of stress incontinence patients are in the perimenopausal age group and are multiparous. Raz[3] has suggested that the female urethral continence mechanism is dependent on the interaction of four urethral factor: urethral closing pressure, urethral length, urethrotrigonal anatomy, and urethral reception of intra-abdominal pressure.

The urethral closing pressure is predominantly a result of the interaction of smooth and striated muscle sphincter activity, but there is also some contribution by nonmuscular urethral factors such as the submucosal vascular plexus, the elastin and collagen content of the urethral tissues, and a sphincter like effect of the mucosa. There has been considerable diversity of opinion regarding the anatomic structure and the innervation of the urethral sphincters, and a variety of views have been expressed in the literature.

Lapides and associates have stressed the importance of urethral length in the maintenance of continence in the female. However, although it certainly interacts with other factors to contribute to continence, a short urethra alone will not produce incontinence. Urethral length varies considerably in normal women, and women with proven genuine stress urinary incontinence do not invariably have urethral shortening.

Urethrotrigonal anatomy, which can be demonstrated by lateral cystourethrography, should fulfill certain criteria. The bladder base should lie above the level of the inferior ramus of the symphysis, and with straining should not descend more than 1.5 cm. There should be a normal urethrotrigonal alignment with an angle normally less than 100 degrees, and the urethral axis should be approximately 35 degrees from the vertical. In the hypermobile situation loss of all of the normal anatomic features may occur, a radiologic finding that correlates with the clinical finding of cystourethrocele. However, clinical experience has shown that the coexistence of cystourethrocele and incontinence does not predict that the incontinence is of a genuine stress variety.

The transmission of intra-abdominal pressure to the intra-abdominal portion of the proximal urethra is also reported to be important in the maintenance of continence. This is a passive phenomenon, and is the result of the normal anatomic configuration just described. Whenever there is a rise in intra-abdominal pressure during such stresses as coughing or straining, the pressure is transmitted not only to the bladder but also to the proximal urethra, with resultant increase in the closing pressure, and prevention of leakage. If the urethral axis is altered, rotational descent will drop the proximal urethra and bladder base from its intra-abdominal location, and will obviously impair such pressure transmission.

A wide variety of operations have been used to correct this condition, generally involving the principles of elevating the bladder neck anteriorly and/or elongating and narrowing the proximal urethra. Two of the most popular operations today for female stress incontinence are the Marshall-Marchetti-Krantz and Birch vesicourethropexies. The Marshall-Marchetti-Krantz technique has at least an eighty-five percent success rate, against which other operative success rates must be measured. Recently, the Pereyra operation and its modifications have enjoyed some popularity, but less than basic techniques.

Notwithstanding the foregoing, however, there remains a need for an improved treatment for SUI. Preferably, the treatment is as noninvasive as possible under the circumstances, and will eliminate or minimize hospitalization and the use of general anesthetics. In addition, there remains a need for improved medical instrumentation such as drill guides and suture passers for use in connection with SUI treatment and other medical procedures.

SUMMARY OF THE INVENTION

In accordance with an aspect of the present invention, there is provided a suture passer of the type adapted for releasably retaining a suture. The suture passer comprises a handle, and an elongate tubular probe guide extending in a distal direction straight or curved from the handle. An elongate probe is axially movably disposed within the tubular probe guide, for motion between a first retracted position and a second extended position in which the sharpened distal tip of the probe is exposed. An annular recess is provided on the probe, to cooperate with an opening on the tubular guide for receiving a suture. The probe is axially movable with respect to the probe guide between a first position in which the annular recess is aligned with the opening for receiving a suture therein, a second position wherein the annular recess is out of alignment with the opening, to trap or retain a suture therein and a third position in which the distal probe tip is exposed.

These and additional features and advantages of the present invention will become apparent from the detailed description of preferred embodiments which follows, when taken together with the attached drawings and claims.

BRIEF DESCRIPTION OF THE DRAWINGS

FIG. 1 is a cross sectional view of a suture passer in accordance with the present invention.

FIG. 1a is a fragmentary cross-sectional view of an alternate embodiment of the suture passer in accordance with the present invention.

FIG. 2 is an enlargement of the distal tip of the suture passer illustrated in FIG. 1.

DETAILED DESCRIPTION OF PREFERRED EMBODIMENTS

Figure 3:
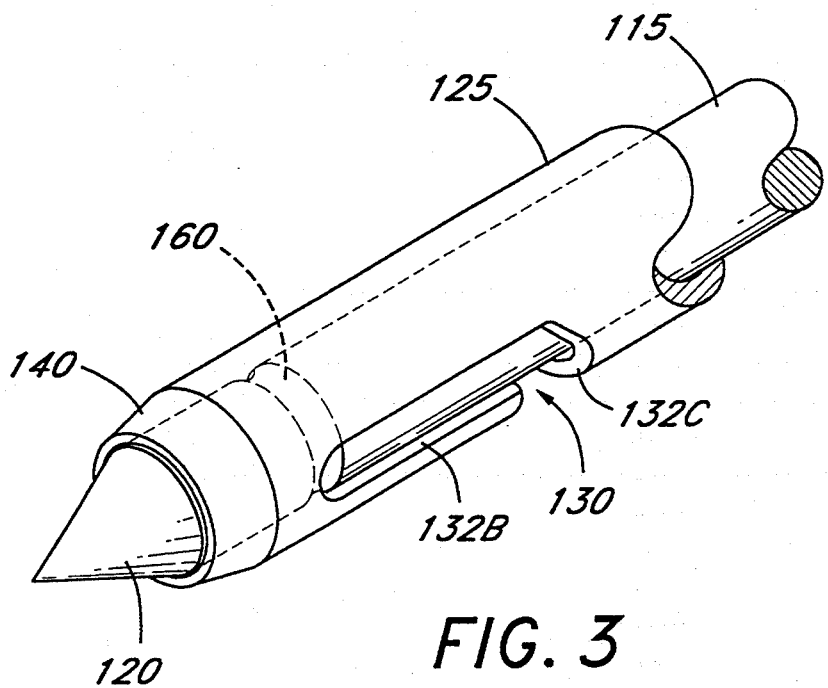
FIG. 3 is a left perspective view of the distal tip of the suture passer illustrated in FIG. 2.

SUI is generally curable with any of a variety of surgical procedures that properly suspends the bladder neck. However, limitations of known procedures include 1) the extent of surgical morbidity 2) the ever present threat of long term failures and 3) the reproducibility between different surgeons.

Pereyra[1] introduced the transvaginal bladder neck suspension as a less invasive alternative to open retropubic procedures. Stamey[2] limited morbidity and improved the reproducibility of the transvaginal bladder neck suspension by introducing endoscopic control and confirmation of suture placement. Raz[3] has improved reproducibility by introducing full palpatory control of needle passage through the retropubic space, thereby limiting disability through injury to the bladder or other retropubic structures.

The distal passage of the suture passer disclosed herein or other needle followed by a sweep back to the bladder neck area described herein accomplishes a similar goal but without the necessity of entering the retropubic space. Passage of the needle point to the level of the introitus along the underside of the pubic bone obviates the need to turn the needle down toward a bladder neck that has been digitally elevated, thereby reducing the risk of bladder injury. Extraction of the needle from the pubourethral ligament is necessary to allow a "capture" of the more pliable pubocervical fascia alongside the urethra. The subsequent, gentle sweep back of the needle along the surface of the pubocervical fascia provides an easy and safe means of introducing the needle to the bladder neck area under the vaginal digital guidance.

Gittes and Loughlin[5] have further popularized the technique of Pereyra and demonstrated an advantage of increased long-term efficacy by creating an autologous bolster with the transvaginal passage of a curved needle. As an alternative manner of creating an autologous bolster, the proposed modification described herein uses the suture passer disclosed herein, or a Stamey needle through a suprapubic approach to carry the suture through all of its vaginal passes. The full carriage of the suture by the suture passer needle offers the benefits of 1) improving accuracy and reproducibility by allowing palpation of the needle at each vaginal entry point in reference to the bladder neck and catheter, 2) potentially decreasing morbidity by reducing the risk of injury and/or irritation through inadvertent entry into any part of the urethra or bladder and 3) possibly contributing to long term efficacy by assuring that a full thickness layer of pubocervical fascia is captured. This technique permits the capture of a large lateral volume of pubocervical fascia similar in an area to that available for suturing in an open retropubic urethropexy.

Leach[4] has limited morbidity by decreasing postoperative pain and has potentially improved long-term efficacy with pubic fixation of the suspending sutures. However, the trochar needle passage through the pubic bone as described by Leach can be difficult through the limited exposure that is used with some forms of endoscopic bladder neck suspension. Other various forms of pubic bone fixation have also been described with transvaginal and open bladder neck suspension surgery[6,7,8]. To facilitate the anchoring of the suspensory suture to the pubic bone with minimal soft tissue dissection, the present inventor has used a new set of devices called the Mitek Anchor System. The latest generation of Mitek anchor, the G2, consists of a titanium body coupled to nickel-titanium arcs. These anchors have recently been used most commonly for tenodesis and ligamentous reconstruction of the shoulder and foot[9,10].

In the present setting of bladder neck suspensions, the Mitek anchor with attached suture is passed into a hole drilled in the pubic bone. Care must be taken to assure that the hole has been drilled into the pubic bone and not inferiorly through the tendon of the adductor longus or superiorly through the rectus fascia over the surface of the In accordance with one aspect of the present invention, there is provided a suture passer adapted for grasping and passing internal sutures, such as to construct the sling disclosed in copending U.S. application Ser. No. 08/042,739, filed Apr. 5, 1993, which is incorporated herein by reference. The suture passer of the present invention is particularly suited for use in connection with such surgery as the bladder suspension procedure disclosed in copending U.S. application Ser. No. 08/042,739, filed Apr. 5, 1993, which is incorporated herein by reference, where sutures are required to be advanced and withdrawn without direct visualization and through relatively long distances. Alternatively, the suture passer may be used with other techniques such as Pereyra, Stamey and Gittes methods.

The suture passer of the present invention enables the clinician to avoid accidental damage to the patient's internal structures and accidental needle sticks to himself and operating room personnel. The passive retraction of the needle point within the cannula, which will be discussed, facilitates the foregoing safety features, and secure capture of the suture material. The ability to advance the cannula with a blunt (retracted needle tip) end also facilitates internal suturing without direct visualization. Safe direct tactile feedback is provided along organ surfaces to localize placement of the suture. These and other features and advantages of the suture passer of the present invention will be discussed below.

Referring to FIG. 1, there is disclosed a suture passer 105 in accordance with one aspect of the present invention. In general, suture passer 105 comprises a handle 110, an axially movable probe 115, and a probe guide 125 having a suture channel 130. Details of suture channel 130 and related structures can be seen in the enlarged view in FIG. 2.

Handle 110 serves both as a gripping area for the user and as a support structure for the suture passer 105. Handle 110 preferably comprises a hollow tubular body having proximal end wall 111 and distal end wall 112. Handle 110 is preferably of such a size to be easily gripped by a user. A handle 110 being at least approximately 0.75 inches (20 mm) in diameter and 4 inches (110 mm) in length has been found to work well. Preferably, handle 110 is provided with knurling or other surface texturing to produce a high friction gripping surface.

A support 135 is preferably mounted such that it extends from the distal end of the handle 110 to provide a mounting support for probe guide 125. The support 135 as illustrated is provided with a generally cylindrical proximal section 137 for engagement within the distal end of the handle 110 and a tapered distal section 139 for securing probe guide 125. The support 135 acts as a transition member from the handle 110 to support the probe guide 125.

The probe guide 125 comprises an elongated tubular member which is at its proximal end inserted within or secured to the support 135. The probe guide 125 may be fixed to the support 135 in any variety of manners, including brazing, threading or others known in the art.

The probe guide 125 extends distally therefrom and is preferably within the range of from about 6 inches to about 8 inches in length and may be straight or curved as illustrated in FIGS. 1 and 1a. The length of probe guide 125 may vary, of course, depending on the exact intended procedure.

At its distal end, the probe guide 125 is provided with a smooth tapered engaging face 140. The distal extreme of tapered face 140 is slightly rounded or polished so that it can be pressed lightly against and swept along the surface of tissue such as the pubocervical fascia without cutting or traumatizing the tissue.

The probe guide 125 is preferably no more than about 0.1 inches (2.5 mm) in diameter and is provided with at least one central lumen for acceptance of an axially movable probe 115. An elongate probe 115 is mounted within the handle 110 and extends through the support 135 and the probe guide 125. Probe 115 is preferably provided at its proximal end with a relatively large diameter body portion 116 adapted for reciprocal motion within tubular handle 110. Body portion 116 is preferably provided with a slightly smaller diameter recessed portion 117 for receiving a return spring 142 which biases the probe in the proximal direction. Alternatively, any of a variety of means can be utilized to provide a proximal bias on probe 115.

The length of body portion 116 is less than the axial length of the cavity within handle portion 110 so that the body portion 116 has an axial range of motion within the range of from about 2 mm to about 10 mm, and preferably about 0.12 inch (3 mm). The proximal end wall 136 of support 135 which extends into the handle 110 acts as one limiting stop for distal travel of body 116. The distal surface of end wall 111 limits proximal travel of body 116. Spring 140 pushes against an annular shoulder 118 on body portion 116, biasing the probe 115 proximally.

The distal end of probe 115 is provided with a sharpened tip 120. Spring 142 normally biases tip 120 towards a first retracted position within the distal end of probe guide. 125. Axial distal force on body portion 116 extends tip 120 into a second exposed position as illustrated in FIGS. 1 and 2. Although the probe 115 may be actuated in any number of ways, such as by use of a knob or button, it is presently preferred that a rotatable cam 122 be used.

The cam 122 is attached to a post 150 which extends proximally from the handle 110. The cam 120 is rotatably mounted about a pin 155 which extends in an axis perpendicular to the longitudinal axis of the probe 115. The proximal end of the body portion 116 has a rod 145 which extends proximally through an opening 147 in the proximal end wall 111 of the handle 110.

The cam 122 has at least a two position engaging surface which, when rotated into position, engages the rod 145 of the body 116. In a first position, the bias imposed by return spring 142 is overcome and the sharpened distal end 120 of probe 115 is extended outwardly from the probe guide 125. In a second engaged position, the distal end 120 remains within probe guide 125, but the suture lock is actuated as will be discussed. In a third position, the distal tip 125 is passively fully retracted within guide 125, and the suture lock is open such as for receiving or releasing a suture.

The cam 120 is preferably provided with an actuator portion 156 which extends radially outwardly and which may be used by the operator for rotating the cam 122.

Figure 4:
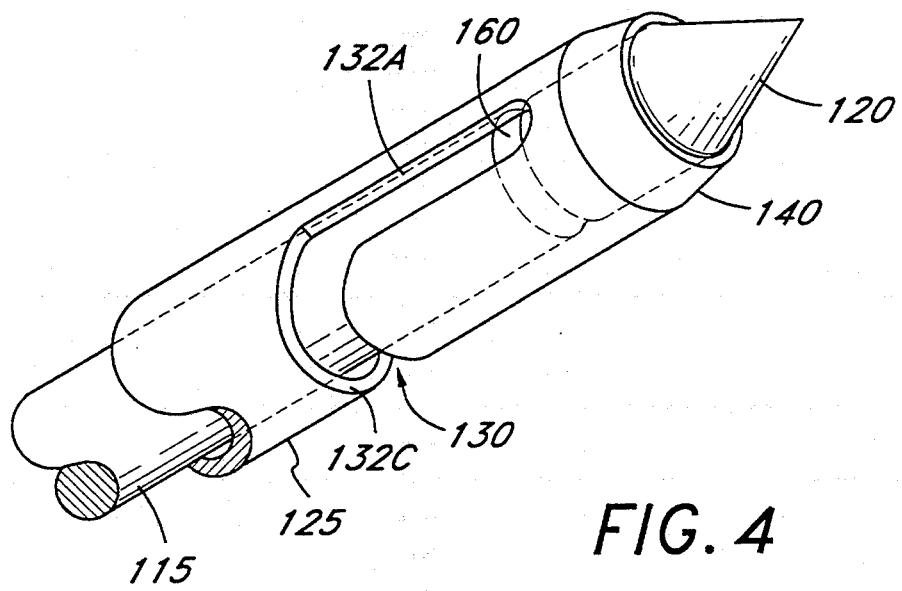
FIG. 4 is a right perspective view of the distal tip of the suture passer illustrated in FIG. 2.

A suture channel 130 is provided near the distal end of probe guide 125. Channel 130 cooperates with an annular or slotted recess 160 near the distal end of the probe 115. Suture channel 130 comprises an opening in the probe guide 125 which extends radially inwardly into the guide 125 and then generally axially along the guide 125 towards the distal end. As seen in FIGS. 2, 3 and 4 the opening comprises a slot in the probe guide 125 having a first segment 132A generally extending axially along a first side of the probe guide 125, a second segment 132B generally extending axially along a second side of the probe guide 125. The second side of the probe guide 125 is generally opposite the first side as seen in FIG. 2. A third segment 132C joins the first segment and the second segment, the third segment extending generally transverse to the longitudinal axis of the probe guide 125. The annular or slotted recess 160 in the probe 115 is located such that when the probe 115 is retracted to the proximal limit, the recess 160 and the opening in the channel 130 are aligned for receiving a suture therein.

At least a portion of the suture channel 130 extends generally axially along the guide 125 such that when a suture 165 is located in the recess 160 of the probe 115, the probe 115 may be extended to an intermediate, "locked" position, or to a distal position in which tip 120 is exposed outside of the probe guide 125. In this extended probe position and at all positions between the proximal and distal limits, the suture 165 is trapped within the recess 160 in the probe 115.

As with the drill guide discussed in copending U.S. application Ser. No. 07/862,847, filed Apr. 3, 1992, which is incorporated herein by reference, it is preferred that this instrument be manufactured from a sterilizable material having sufficient rigidity for its intended purpose. Many acceptable materials are well known in the art, such as stainless steel for the needle and needle guide, and stainless steel or a plastic for the handle portion.

The suture passer 105 is operated first by rotating the cam 122 that engages the rod 145 and extends the probe end 120 distally of the probe guide 125. The passer 105 is then extended into a patient's body by gripping the handle 110 and pushing the free end of the probe guide 125 into the body and through the layers of tissue in the same manner as the Stamey needle discussed in and illustrated in copending U.S. application Ser. No. 08/042,739, filed Apr. 5, 1993, which is incorporated herein by reference. The cam 122 is then released and rotates to its neutral position 148 via action of spring 142 against the body 116 in turn pressing the rod 145 proximally against the cam ramp 149. The probe end 120 is thereby retracted into the probe guide 125 so that the suture passer can be manipulated without injury to surrounding tissue while keeping the suture 165 trapped in channel 130.

The suture passer 105 is then guided as discussed and illustrated in copending U.S. application Ser. No. 08/042,739, filed Apr. 5, 1993, which is incorporated herein by reference, to the desired capture point and the cam 122 rotated to a position in which the suture channel 130 is aligned with the recess 160 of the probe 115.

A length of suture 165 is transvaginally introduced at the introitus and digitally pressed against the outside of the probe guide 125 at a point proximal to the suture channel opening 130.

The suture 165 is then moved proximally until the suture 165 falls into the channel opening 130 and the annular or slotted recess 160 on the probe 115. The cam 122 is then released so that rod 145 slides down cam ramp 149 under the bias of spring 142. At this time, the suture 165 is held securely within the channel 130, and distal tip 120 is retracted within guide 125. Preferably, channel 130 and recess 160 are dimensioned so that the suture 165 is slidably retained therein. The passer 105 may then be retracted from the body, thus drawing the suture 165 from inside the body. The construction of a bladder neck suspension web utilizing the suture passer will become apparent from the method disclosed in copending U.S. application Ser. No. 08/042,739, filed Apr. 5, 1993, which is incorporated herein by reference.

Although this invention has been described in terms of certain preferred embodiments, other embodiments that are apparent to those of ordinary skill in the art in view of the foregoing are also within the scope of this invention. Accordingly, the scope of the invention is intended to be defined only by reference to the appended claims.

REFERENCES

[1] Pereyra, A. J.: A simplified surgical procedure for the correction of stress incontinence in women. West. J. Surg., 67:223, 1959.

[2] Stamey, T. A.: Endoscopic Suspension of the vesical neck for urinary incontinence in females: Report on 203 consecutive patients. Ann. Surg., 192:465, 1980.

[3] Raz S.: Modified bladder neck suspension for female stress incontinence. Urology, 1782, 1981.

[4] Leach, G. E.: Bone fixation technique for transvaginal needle suspension. Urology, 31:388, 1988.

[5] Gittres, R. F. and Loughlin, K. R.: No-incision pubovaginal suspension for stress incontinence. J. Urol. 138:568, 1987.

[6] Winter, C. C.: Peripubic urethropexy for urinary stress incontinence in women. Urology, 20:408, 1982.

[7] McKiel, C. F., Jr., Graf, E. C. and Callahan, D. H.: Marshall-Marchetti procedure: modification. J. Urol., 96:737, 1966.

[8] Hancock, R., Brandstetter, L. H. and Hodgins, T. E.: Transpubic suspension of the bladder neck for urinary incontinence. J. Urol., 123:667, 1980.

[9] Richmond, J. C., Donaldson, W. R., Fu, F. and Harner, C. D.: Modification of the Bankart reconstruction with a suture anchor: report of a new technique. Am. J. Sports Med., 19:343, 1991.

[10] Pederson, B., Tesoro, D., Wertheimer, S. J. and Coraci, M.: Mitek anchor system: a new technique for tenodesis and ligamentous repair of the foot and ankle. J. Foot Surg., 30:48, 1991.

[11] Spencer, J. R., O'Conor, V. J. and Schaeffer, A. J.: A comparison of endoscopic suspension of the vesical neck with suprapubic vesicourethropexy for treatment of stress urinary incontinence. J. Urol., 137:411, 1987.

[12] Araki, T., Takamoto, H., Hara, T. Jujimoto, H., Yoshida, M. and Katayama, Y.: The loop loosening procedure for urination difficulties after Stamey suspension of the vesical neck. J. Urol., 144: 1990.

[13] Webster, G. D. and Kreder, K. J.: Voiding dysfunction following cystourethropexy: Its evaluation and management. J. Urol., 144:1990.

I claim:

1. A suture passer of the type adapted for releasably retaining a suture, comprising:
   a handle;
   an elongate tubular probe guide extending in a distal direction from the handle;
   an elongate pointed probe axially movably disposed within the tubular probe guide to facilitate penetration of tissue; and
   a recess on the pointed probe and an opening on the tubular probe guide for receiving a suture, wherein the pointed probe is axially movable with respect to the probe guide between a first position in which the recess is aligned with the opening for receiving a suture therein, and a second position wherein the recess is out of alignment with the opening to trap a suture within the recess, wherein the opening comprises a slot having a first segment generally extending axially along a first side of the probe guide, a second segment generally extending axially along a second side of the probe guide, said second side being generally opposite said first side, and a third segment joining said first segment and said second segment, said third segment extending transverse to the longitudinal axis of the probe guide.

2. A suture passer as in claim 1, further comprising a third position so that in a first position the recess is aligned with the opening for receiving a suture and the distal tip of the pointed probe is retracted within the probe guide; in a second position the recess is out of alignment with the opening and the distal tip of the pointed probe is retracted; and in a third position the recess is out of alignment with the opening and the distal tip of the pointed probe is extended beyond the probe guide.

3. A suture passer as in claim 2, further comprising a control on the handle for selectively positioning the pointed probe in the first, second, and third positions.

4. A suture passer as in claim 3, further comprising an axially movable actuator pin extending proximally from the pointed probe.

5. A suture passer as in claim 4, wherein the control comprise a rotatable cam having a contoured engagement surface for engaging the actuator pin and holds the actuator pin in a stable position.

6. A suture passer as in claim 5, wherein the engagement surface comprises a ramp which cooperates with the actuator pin and the proximal bias on the pointed probe so that the distal tip of the pointed probe is normally retracted within the distal end of the probe guide, and distally extended beyond the probe guide only during manual manipulation of the control.

7. A suture passer as in claim 6, further comprising an indicium on the control for indicating the axial position of the pointed probe.

8. A suture passer as in claim 7, wherein the indicium comprises the rotational position of the cam.

9. A suture passer as in claim 1, wherein said recess comprises an annular or slotted recess extending radially inwardly about the periphery of the pointed probe.

10. A suture passer as in claim 1, further comprising a spring within the handle for biasing the pointed probe in the proximal direction with respect to the probe guide.

11. A suture passer as in claim 1, wherein the distal end of the probe guide is provided with a blunt atraumatic tip which allows for tactile positioning digitally.

12. A suture passer as in claim 1, wherein said third segment joins the proximal ends of said first and second segments of the opening.

13. The suture passer as in claim 1, in combination with a suture extending through the recess on the pointed probe.

14. A suture passer of the type adapted for releasably retaining a suture, comprising:
 a handle;
 an elongate, curved tubular guide extending in a distal direction from the handle, the distal end of the guide having a blunt atraumatic tip that allows for tactile positioning;
 an elongate, curved probe axially movably disposed within the tubular guide to facilitate penetration of tissue; and
 a generally transverse recess on the probe and an opening on the tubular guide for receiving a suture, wherein the probe is axially movable with respect to the guide between a first position in which the recess is aligned with the opening for receiving a suture therein, and a second position wherein the recess is out of alignment with the opening to trap a suture within the recess.

15. A suture passer of the type adapted for releasably retaining a suture, comprising:
 a handle;
 an elongate tubular probe guide extending in a distal direction from the handle;
 an elongate pointed probe axially movably disposed within the tubular probe guide to facilitate penetration of tissue;
 a recess on the pointed probe and an opening on the tubular probe guide for receiving a suture, wherein the pointed probe is axially movable with respect to the probe guide between a first position in which the recess is aligned with the opening for receiving a suture therein and the distal tip of the pointed probe is retracted within the probe guide, a second position in which the recess is out of alignment with the opening to trap a suture within the recess and the distal tip of the pointed probe is retracted, and a third position in which the recess is out of alignment with the opening and the distal tip of the pointed probe is extended beyond the probe guide;
 an axially movable actuator pin extending proximally from the pointed probe; and
 a control on the handle for selectively positioning the pointed probe in the first, second, and third positions, said control comprising a rotatable cam having a contoured engagement surface for engaging the actuator pin and holding the actuator pin in a stable position.

16. A suture passer as in claim 15, wherein the engagement surface comprises a ramp which cooperates with the actuator pin and the proximal bias on the pointed probe so that the distal tip of the pointed probe is normally retracted within the distal end of the probe guide, and distally extended beyond the probe guide only during the manual manipulation of the control.

17. A suture passer as in claim 16, further comprising an indicium on the control for indicating the axial position of the pointed probe.

18. A suture passer as in claim 17, wherein the indicium comprises the rotational position of the cam.

* * * * *